United States Patent
Vogel et al.

(10) Patent No.: US 9,636,047 B2
(45) Date of Patent: May 2, 2017

(54) DEVICE FOR HEIGHT MEASUREMENT

(71) Applicant: SECA AG, Reinach BL (CH)

(72) Inventors: Frederik Vogel, Hamburg (DE); Marc-Oliver Von Maydell, Hamburg (DE)

(73) Assignee: SECA AG, Reinach BL (CH)

( * ) Notice: Subject to any disclaimer, the term of this patent is extended or adjusted under 35 U.S.C. 154(b) by 246 days.

(21) Appl. No.: 14/114,600

(22) PCT Filed: Oct. 17, 2012

(86) PCT No.: PCT/DE2012/001025
§ 371 (c)(1),
(2) Date: Oct. 29, 2013

(87) PCT Pub. No.: WO2013/071904
PCT Pub. Date: May 23, 2013

(65) Prior Publication Data
US 2014/0071270 A1  Mar. 13, 2014

(30) Foreign Application Priority Data

Nov. 15, 2011  (DE) .................. 10 2011 118 810

(51) Int. Cl.
*A61B 5/00* (2006.01)
*A61B 5/107* (2006.01)

(52) U.S. Cl.
CPC .......... *A61B 5/1072* (2013.01); *A61B 5/1079* (2013.01)

(58) Field of Classification Search
CPC ................... A61B 5/1072; A61B 5/1079
USPC .............................................. 348/135
See application file for complete search history.

(56) References Cited

U.S. PATENT DOCUMENTS

| | | | |
|---|---|---|---|
| 2005/0007878 A1* | 1/2005 | Chen | A42B 1/24 367/99 |
| 2005/0171451 A1* | 8/2005 | Yeo et al. | 600/547 |
| 2010/0081895 A1* | 4/2010 | Zand | A61B 5/0002 600/309 |
| 2010/0298708 A1 | 11/2010 | Pan | |
| 2010/0312143 A1* | 12/2010 | Kim | 600/587 |

FOREIGN PATENT DOCUMENTS

| | | |
|---|---|---|
| DE | 202010016423 | 2/2011 |
| WO | 2011127578 | 10/2011 |
| WO | WO 2011127578 A1 * | 10/2011 |

* cited by examiner

*Primary Examiner* — Jeffery Williams
(74) *Attorney, Agent, or Firm* — Lucas & Mercanti, LLP; Klaus P. Stoffel

(57) ABSTRACT

A device for measuring the body height of a person. In the area of an inner border of a building room at least one emitter for emitting a primary signal and at least one sensor for picking up a measuring signal are arranged. The emitter, as well as the sensor, is coupled to a control device. The control device is coupled to a display device.

7 Claims, 6 Drawing Sheets

DEVICE FOR HEIGHT MEASUREMENT

The present application is a 371 of International application PCT/DE2012/001025, filed Oct. 17, 2012, which claims priority of DE 10 2011 118 810.3, filed Nov. 15, 2011, the priority of these applications is hereby claimed and these applications are incorporated herein by reference.

BACKGROUND OF THE INVENTION

The invention relates to a device for measuring the height of the body of a person.

For measuring the body height of a person, frequently so-called height measuring rods are used which, for example, are provided in a self-supporting manner with a base part, or are mounted on a wall. The person to be measured typically stands with his/her back against this height measuring rod, and an exact head positioning is predetermined by a so-called head stop. As a result, the person to be measured comes into body contact with the measuring device which is frequently perceived as unpleasant or at least undesirable.

Also already known are contactless height or spacing measurement devices which are placed in the area of the floor of a room. This makes it possible to determine distances, for example, through an ultrasound measurement.

SUMMARY OF THE INVENTION

It is the object of the present invention to construct a device of the above mentioned type in such a way that a contactless measurement of the body height is supported, while the operation remains simple.

In accordance with the present invention, this object is met in that in the area of an inner border of a room of a building at least one emitter for emitting a primary signal, and at least one sensor for receiving a receiving signal are arranged, and the emitter as well as the sensor are coupled to a control device which is coupled to a display device.

In connection with the present invention, the term sensor is to be understood inclusively. In particular, it is being considered that the sensor can consist of one or several transmitters as well as one or more receivers. It is also possible to realize the function of the transmitter and of the receiver in the area of the sensor as a single component.

By arranging the emitter as well as the sensor in the area of the inner border of a room of a building, a stationary device is made available which supports a very operator friendly use. In particular, the emitter, as well as the sensor, is arranged outside of areas which are typically subject to contamination. Accordingly, the device for contactless measurement of the body height is also especially suitable for use in physicians' offices or hospitals where particularly high requirements are made with respect to cleanliness.

Additional information with respect to the person to be measured can be made available by providing the device additionally with scales for determining the weight of the person to be measure. For adapting to spatial conditions, it is proposed to construct the control device for evaluating a reference measurement which takes into consideration the distance of the sensor from the area where the person stands.

In accordance with a typical embodiment, it is provided that the sensor is arranged in the area of a ceiling of the room.

In accordance with another embodiment, it is also possible that the sensor is arranged in an area of a wall of the room.

An individual adaptation to spatial conditions which are actually present is supported by the fact that the sensor is installed with the use of a support member.

For supporting measurement results which are as precise as possible, it is proposed that a projector for projecting a location marking to indicate where the person is to be measured, is used.

In the drawings, embodiments of the invention are schematically illustrated. In the drawings:

DETAILED DESCRIPTION OF THE INVENTION

Figure 1:
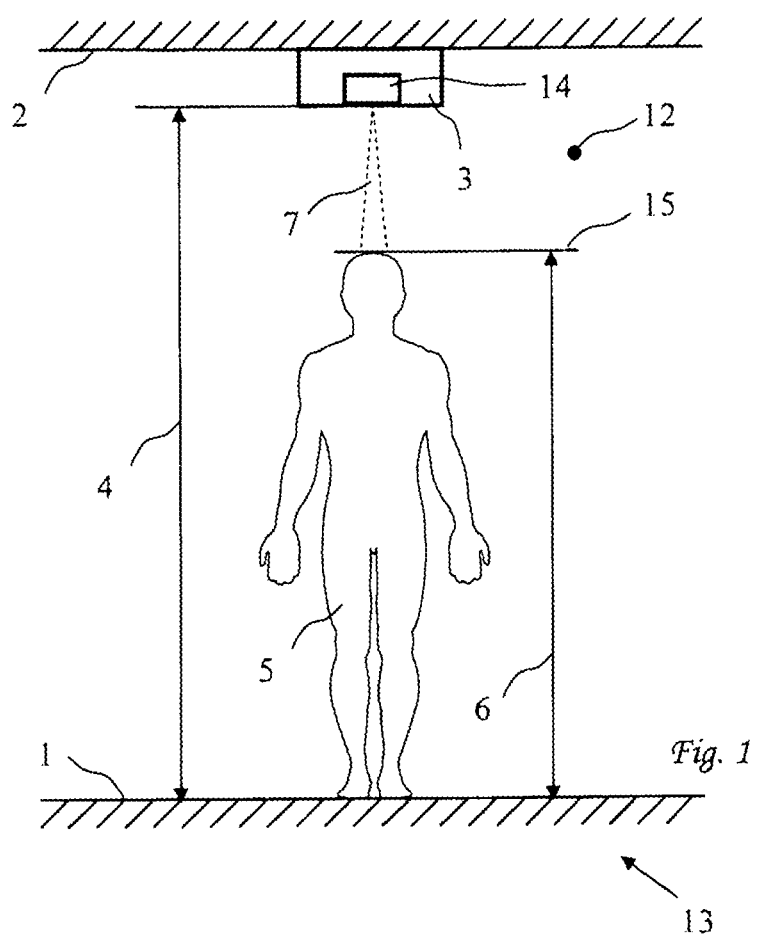
FIG. 1 is a schematic illustration of a side view of a measuring device arranged in the area of a building ceiling as well as of a person to be measured.

In accordance with the embodiment illustrated in FIG. 1, an interior space 12 of a building 13 is at least over portions thereof defined by a floor 1 and a ceiling 2. In the area of the ceiling 2, in the illustrated embodiment, an emitter 14 and at least one sensor 3 are arranged. When carrying out length or distance measurements with the use of the emitter 14 as well as the sensor 3, a spacing 4 between the sensor 3 and the floor 1 must be taken into consideration. An upper limitation 15 of a head of the person 5 to be measured has, relative to the floor 1, a distance which corresponds to the body height 6 to be determined.

Figure 5:
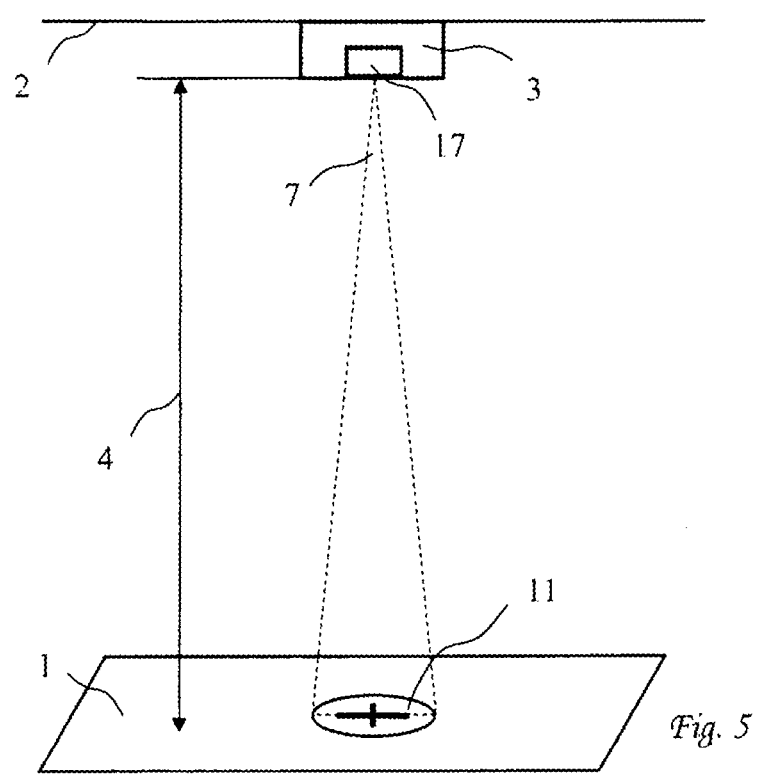
FIG. 5 shows a modification of the measuring device according to FIG. 1 with the use of an additional projection device for generating a marking in the area of a floor of the building.

FIG. 1 and FIG. 5 also show as an example a typical acquisition range 7 of the sensor 3.

Figure 2:
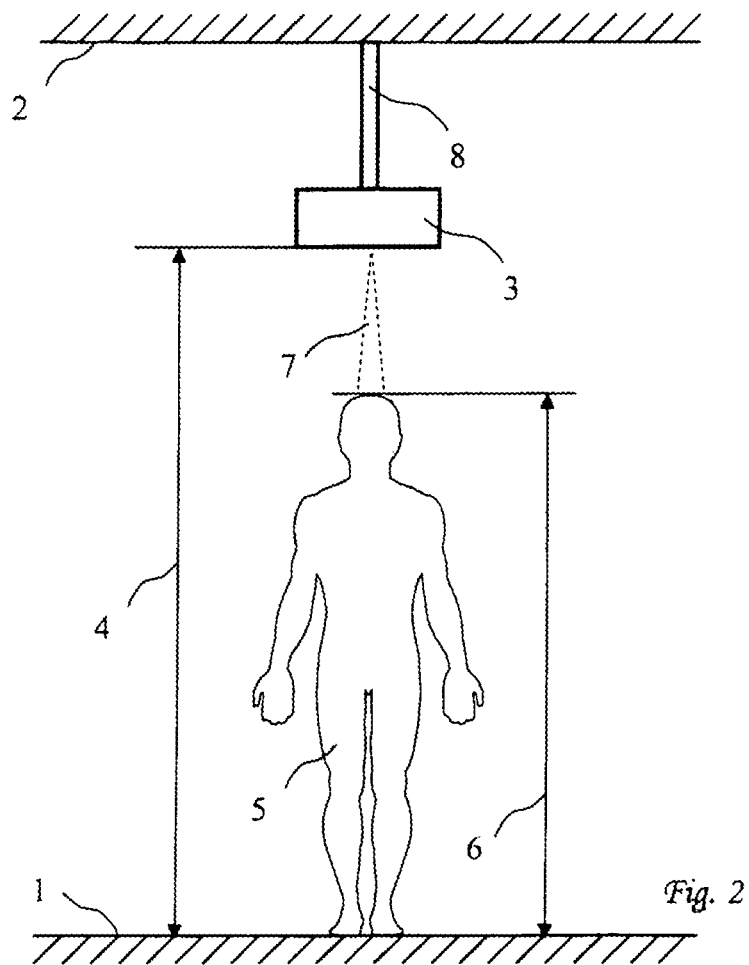
FIG. 2 shows the arrangement according to FIG. 2 with the additional use of a frame for the measuring device.

FIG. 2 shows an embodiment which is modified as compared to FIG. 1 with the additional use of a spacer piece 8 for supporting the sensor 3. For example, the spacer piece 8 can be used in cases of ceiling heights which would lead to too large a distance between the sensor 3 and the person 5 to be measured. However, in modified embodiments, the spacer piece 8 can also be constructed generally as a support for the sensor 3 and/or the emitter 14.

Figure 3:
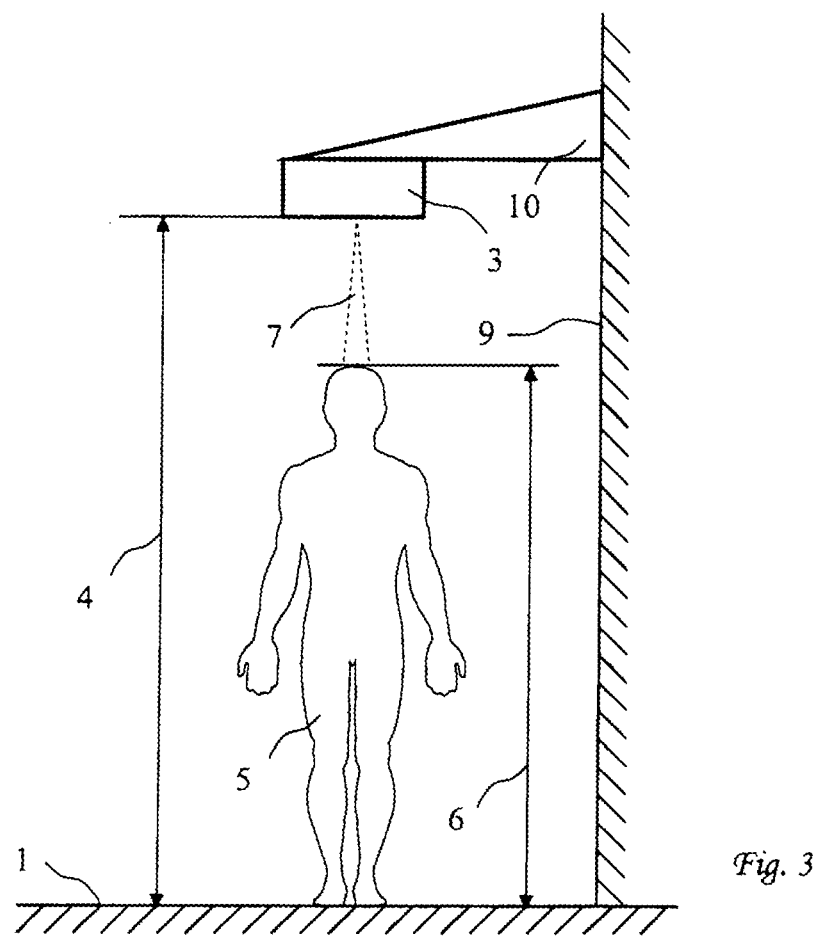
FIG. 3 is a schematic illustration of an additional embodiment in which the measuring device is mounted in the area of a wall of the building.

FIG. 3 shows another embodiment in which the sensor 3 is mounted in the area of a wall 9 of the building 13. The illustrated embodiment shows fastening of the sensor 3 with the use of a wall support 10. In accordance with the embodiment in FIG. 3, similar to the embodiments in FIGS. 1 and 2, a measurement of the body height takes place with an acquisition direction directed vertically downwardly. Accordingly, the wall support 10 serves essentially for suitably positioning the sensor 3.

Figure 4:
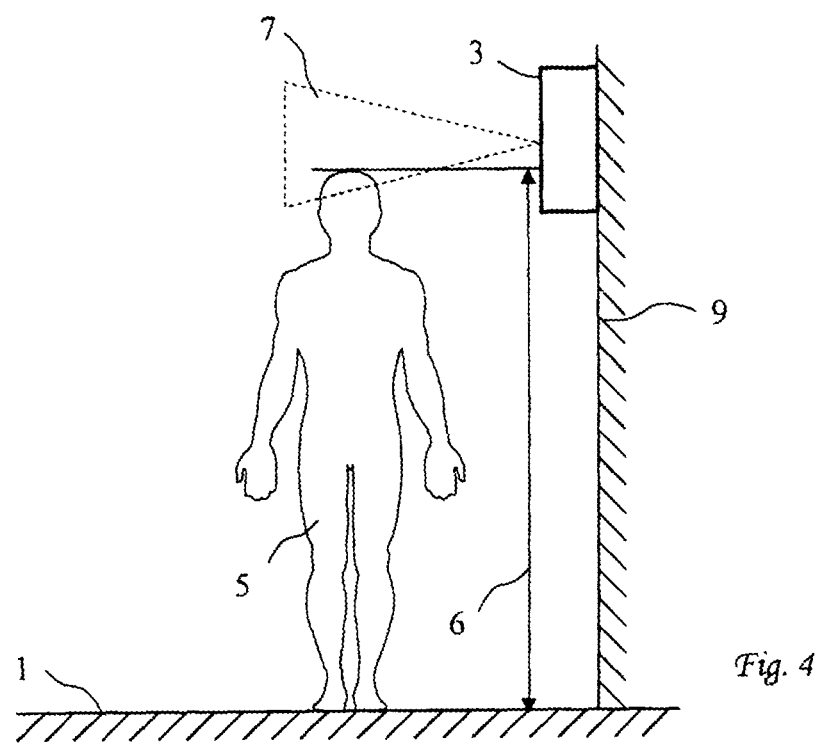
FIG. 4 shows another embodiment with a measuring device for laterally measuring in an area of a measuring device arranged in the area of a building wall.

In accordance with the embodiment in FIG. 4, the acquisition range 7 is aligned with a horizontal component starting from the sensor 3. Accordingly, a lateral measurement of the body height of the person 5 to be measured takes place.

In accordance with the embodiment in FIG. 5, a projector 17 is used which projects a marking 11 into the area of the floor 1. The marking secures an optimum standing point for the person 5 to be measured.

A projector for marking may be arranged, for example, in the vicinity of the sensor 3. Moreover, it is also possible that a projection of the marking can take place from the side. A projection from the side avoids shading of the marking by the person to be measured when stepping on the marking. When the projector is arranged in the area of the sensor 3, the projector can be integrated into the housing of the sensor 3.

Figure 6:
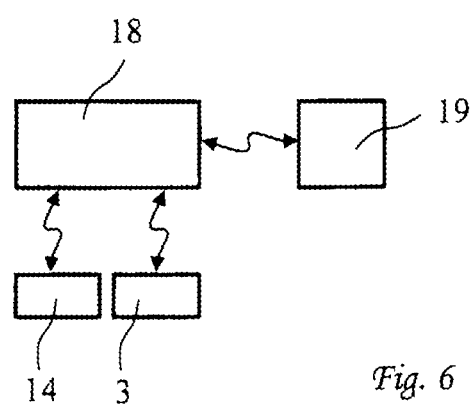
FIG. 6 is a schematic block diagram for illustrating the coupling of the emitter and the sensor with a control device, as well as the use of an indicating device.

FIG. 6 schematically shows a coupling of the emitter 14 and the sensor 3 with a control device 18. Coupling takes place preferably without contact through a radio/transmission distance or an optical coupling. Moreover, the control device 18 is coupled to an indicating unit 19. Also in this case, the coupling takes place without contact.

For example, the display of a computer may be used as the indicating device 19. However, it is also possible to use portable devices to be held by hand, for example, corresponding to a mobile phone or a remote control.

In dependence on the respective case of application, the emitter 14 can emit various primary signals, for example, ultrasound, radar waves or a laser beam. It is further possible to construct the emitter 14 merely as an illuminating device and to use as a sensor 3 a camera which is coupled preferably to a control device which is equipped for carrying out pattern recognition.

As an alternative to the use of a special projector 17 for generating a marking 11 in the area of the floor 1, for example, with the use of a red laser beam, it is also possible to glue the marking 11 for example, to the floor 1 or to produce a permanent connection in another manner.

As a result of the determination of the distance 4 by means of measuring technology as the room height to be taken into consideration, the measuring device can be used in rooms having different heights, and the control device 18 can take into consideration the determined length reference as a correction value. It is also possible, for example, to take into consideration a drift of the sensor 3 due to temperature changes or changes of the humidity as a result of one or more reference measurements. These correction values can also be taken into consideration for the exact determination of the respective body height of the person 5 to be measured.

In lateral length measurements a triangulation can be used, for example.

An energy supply of the device components used can be effected through the existing power grid or through batteries or photovoltaically. Directed wireless energy transmissions can also be used.

In addition to the advantages already explained with respect to adhering to requirements concerning hygiene, the measuring device according to the invention avoids special mounting devices and a place required for storing the devices for this purpose. Moreover, it is also not necessary to clean or disinfect the measuring device because no contact with the body of the user occurs.

In particular, in a combination of the measuring device with a scale, it is also possible to adapt in already installed scales the installation location of the emitter 14 and/or of the sensor 3 to the already existing positioning of the scale.

The invention claimed is:

1. A device for measuring body height of a person, comprising: at least one emitter for generating a primary ultrasound signal; at least one sensor for picking up a measuring ultrasound signal, the emitter and the sensor being arranged in a common geometric area of an inner border of a building room; a control device, the emitter as well as the sensor being coupled to the control device without contact; a display device coupled to the control device, wherein the sensor is arranged above the person in the vertical direction in the area of a ceiling of the room; and a projector for projecting a location marking below the sensor in the vertical direction on a floor of the room for the person to be measured so that a vertical connecting line extends from the location marking through the person to the sensor during a measurement operation, wherein the control device carries out reference measurements using the emitter and the sensor to take into consideration temperature changes and/or humidity changes, and further carries out a measurement of a distance between the floor and the sensor.

2. The device according to claim 1, further comprising a scale for measuring weight of the person to be measured.

3. The device according to claim 1, wherein the control device is constructed for evaluating a reference measurement which takes into consideration a distance of the sensor from a surface on which the person to be measured stands.

4. The device according to claim 1, wherein the sensor is arranged in the area of a wall of the room.

5. The device according to claim 1, further comprising a support on which the sensor is mounted.

6. The device according to claim 1, wherein the sensor is over at least portions thereof formed by at least one camera.

7. The device according to claim 6, wherein a lateral triangulation is realized.

* * * * *